United States Patent [19]

Hiruma et al.

[11] Patent Number: 5,880,343
[45] Date of Patent: Mar. 9, 1999

[54] GRASS AND METHOD OF INTRODUCING ENDOPHYTIC FUNGI INTO A GRASS

[75] Inventors: Naoya Hiruma; Satoshi Shinozaki, both of Fujinomiya, Japan

[73] Assignee: Mayekawa Manufacturing Co., Ltd., Tokyo, Japan

[21] Appl. No.: 661,774

[22] Filed: Jun. 11, 1996

[30] Foreign Application Priority Data

Jun. 15, 1995 [JP] Japan .................................. 7-172906
Aug. 14, 1995 [JP] Japan .................................. 7-228506

[51] Int. Cl.$^6$ ........................... A01H 17/06; A01H 5/00;
A01H 1/00
[52] U.S. Cl. ......................... 800/320; 800/298; 800/295;
800/302; 47/58.1
[58] Field of Search .................................. 800/200, 250,
800/DIG. 8, DIG. 55, DIG. 56, DIG. 57,
DIG. 58; 47/58

[56] References Cited

U.S. PATENT DOCUMENTS

| | | |
|---|---|---|
| 4,940,834 | 7/1990 | Hurley et al. . |
| 5,415,672 | 5/1995 | Fahey et al. .............................. 47/57.6 |
| 5,723,720 | 3/1998 | Brede et al. ............................ 800/200 |

FOREIGN PATENT DOCUMENTS

| | | |
|---|---|---|
| 73853 91 | 10/1991 | Australia . |
| B-73853/91 | 10/1991 | Australia . |
| WO96/39807 | 12/1996 | WIPO . |

OTHER PUBLICATIONS

Handbook of Integrated Pest Management for Turf and Ornamentals (Ed.: A.R. Leslie), 1994, Boca Raton, Fl., pp. 521–528, M.L. Fraser & J.P. Breen: "The Role of Endophytes in Integrated Pest Management of Turf".

Ann. Appl. Biol, vol. 107, 1985, pp. 17–24, G.C.M. Latch & M.J. Christensen: "Artificial infection of grasses with endophytes".

Proc. of the 2nd Int. Symp. on Acremonium/Grass Interactions 1992 (D.E. Hume, G.C.M. Latch & G.M. Latch: "Infection of plantlets derived from ryegrass and tall fescue meristems with Acremonium endophytes."

Plant Disease, vol. 70, No. 5, 1986, pp. 380–382, M.C. Johnson, L.P. Bush & M.R. Siegel: "Infection of tall fescue with acremonium coenophialum by means of callus culture."

Biotechnology of Endophytic Fungi of Grasses (Ch. W. Bacon & J.F. White, Eds.), 1994, Boca Raton, Fl., pp. 201–209, C. Reed Funk, F. C. Belanger & J.A. Murphy: "Role 0f endophytes in grasses used for turf and soil conservation." Infection of plantlets derived from rygrass and tall fescue meristems ith Acremonium endophytes.

Sah et al. Virulence patterns of geographically differing isolates of *Pyrenphora tritici–repentis* and sources of resistance in wheat. Plant Disease. 76:712–716, 1992.

White et al. Endophyte–host associations in grasses. XXII. Conidia formation by Acremonium endophytes on the phylloplanes of *Agrostis hiemalis* and *Poa rigidfolia*. Mycologia. 88:174–178, 1996.

Porter et al. Indole alkaloids from *Balansia epichloe* (Weese). Journal of Agricultural Food Chemistry. vol. 25, pp. 88–93, 1977.

Francl. Refined procedures for inoculating wheat seedlings with *Pyrenophora tritici–repentis* and rating their reactions. Plant Disease. 78:745–748, 1994.

Johnson et al. Infection of tall fescue with *Acremonium coenifolium* by means of callus culture. Plant Disease. 70:380–372, 1986.

Nielsen et al. Regeneration of green plants from embryogenic suspension cultures of Kentucky bluegrass (*Poa pratensis* L.) Journal of Plant Physiology. 141:589–595, 1993.

O'Sullivan et al. Infection of plantlets, dervied from ryegrass and tall fescue meristems, with *Acremonium endophytes*. Proceedings from the Second Internation Acremonium–Grass Interactions. pp. 16–17, 1993.

Funk et al. Importance of Acremonium endophytes in turfgrass breeding and management. Agric. Ecosystems Environ. vol. 44 pp. 215–232, 1993.

Johnson et al. Infection of Tall Fescue with Acremonium coenophialum by Means of Callus Culture. Plant Disease. vol. 70 pp. 380–382, 1986.

Nielsen et al. Regeneration of green plants from embryogenic suspension cultures of Kentucky bluegrass (*Poa pratensis* L.) Journal of Plant Physiology. vol. 141 pp. 589–595, 1993.

O'Sullivan et al. Infection of plantlets, derived from rylegrass and tall fescue meristems, with Acremonium endophytes. Proceedings of the Second International Acremonium– Grass Interactions. Hume, Latch and Easton, eds. pp. 16–17, 1993.

*Primary Examiner*—Douglas W. Robinson
*Assistant Examiner*—Melissa L. Kimball
*Attorney, Agent, or Firm*—Kanesaka & Takeuchi

[57] ABSTRACT

To provide a grass having improved characteristics, an endophyte having endophytic fungi which produce an insect-resistant alkaloid is artificially introduced into a grass by inoculation so that the endophyte lives in and infects the grass.

8 Claims, 2 Drawing Sheets

GRASS AND METHOD OF INTRODUCING ENDOPHYTIC FUNGI INTO A GRASS

BACKGROUND OF THE INVENTION

1. Field of the Invention

This invention is concerned with grass into which endophytic fungi have been artificially introduced, and to a method of introducing endophytic fungi into grass. Herein, the endophytic fungi comprised of filamentous bacteria will be referred to hereafter as endophytes.

2. Description of the Related Art

Conventional methods of cultivating and growing grasses include the artificial crossing method, selection method, mutation method, cell fusion method and gene insertion method. Due to recent progress in biotechnology, the cultivation period which previously required 10 years or more, has been reduced to several years. As regards genetic insertion, several techniques exist such as a method using agrobacterium, the electroporation method and the particle gun method, and they are now being applied to a large variety of crops.

However, in the case of grasses which produce staple crops, it has been pointed out that this genetic insertion is extremely inefficient. It is difficult to infect grasses using the agrobacterium method, so genetic insertion is very difficult. As regards the electroporation method, a regeneration system has to be developed from the protoplast of the grass, and even if such a regeneration is possible, the characteristics of the plant may suffer damage due to growth mutations.

Concerning the particle gun method, since genes are introduced randomly into the plant organism or culture, the plant obtained frequently becomes a chimera.

In the case of grasses, cell culture techniques such as cell fusion or genetic insertion require complex operating procedures and as they are not very efficient, there are very few examples where they have successfully been applied efficiently and, there are very few instances where they have been successfully developed on a practical level.

Bluegrasses known in the art include Kentucky bluegrass, Canada bluegrass, rough meadow grass, bulbous meadow grass, alpine meadow grass, wavy meadow grass, wood meadow grass, Balforth meadow grass, swamp meadow grass, broad leaf meadow grass, narrow leaf meadow grass, smooth meadow grass, spreading meadow grass and flattened meadow grass.

These plants are members of the group Pooideae, and also belong to the genus Poa which is a part of Poeae. Kentucky bluegrass, for example, is known by the name of *Poa pratensis*. *Poa pratensis* is a plant classified by Clayton et al (*Genera Graminium,* Grasses of the World, 1986).

Bluegrasses of the grass family, which comprises many types of grasses, are typified by Kentucky bluegrass. They are important to man, and are found in meadow and pasture.

Bluegrasses have a wide utility, and as they cover very large areas, they are subject to damage from disease or pests. Damage due to bluegrass worm (Japanese name Shibata moth) is severe, and in areas where pesticide sprays have not reached, grass can disappear overnight as soon as the larvae have hatched.

However, there are some wild plants in nature in which filamentous internal fungi, i.e. endophytes, live together with the plant. They grow particularly well in the gaps between cells, i.e. the intercellular spaces.

These endophytes, or symbiotic filamentous fungi, not only have no adverse effect on the host plant but in fact provide it with useful substances, and contribute to helping withstanding environmental stresses.

Enhancement by endophytes of plant properties is known from the literature, e.g. insect resistance (Siegel et al, 1987 Ann. Rev. Phytopathol. 25: 293–315), disease resistance (Gwinn and Gavin, 1992, Plant Disease 76: 911–914), environmental stress (drought, etc.) resistance (Arachevalta et al, 1989 Agron J. 81: 83–90), and growth enhancement (Latch et al, 1985, N.Z.J. Agric. Res. 28: 165–168). It is particularly well-known that, in perennial rye grass infected with endophytes, these endophytes improve insect resistance due to the repelling substances and alkaloids they produce.

Latch et al in New Zealand are searching for an endophyte known as an endosafe which has a low toxicity to livestock and excellent insect resistance by collecting and studying endophytes in perennial rye grass.

However, many of the plants in which these endophytes live have little utility, so it is necessary to introduce them into useful grasses. In this regard, attempts have already been made to introduce endophytes into perennial rye grass which is an important pasture grass. The techniques used may be broadly distinguished as artificial crossing and artificial inoculation.

In artificial crossing, useful characteristics are introduced by pollen using a plant infected by an endophyte as mer. However, in the conventional method, there were limitations on the species and strains which could be crossed with one another. In artificial inoculation, plants or culture tissues are inoculated with endophytes that have been isolated and cultivated.

The inoculation method is capable of introducing a wider range of types, but due to problems of technique regarding cultivation of endophytes, inoculation conditions and conditions of the plant itself, it is limited to perennial rye grass. To increase the infection rate, a method has been reported where callus is used as the plant tissue which is inoculated. However according to this method, it is necessary to develop a plant regenerating system from the callus, hence the method was still limited to perennial rye grass.

The conventional cell cultivation method involves a troublesome procedure and requires considerable training. Its practical application was moreover difficult since culture mutations caused by transformation or cell fusion had an effect on the characteristics being introduced or on other traits.

In the genetic insertion method, it was not possible to introduce specific characteristics if it was not known which genes had an effect on the characteristics and type of plant.

Characteristics related to complex factors such as environmental stress could not be introduced by techniques such as genetic insertion. Moreover, plants grown by cell culture techniques were often found to exhibit decreased seed fertility. In the case of grasses this led to a decline of yield and was therefore fatal.

In view of the above, growth techniques using endophytes or improvement of characteristics is a totally new approach to solve the above problems.

When endophytes are introduced into plants by artificial crossing, the type of plant is limited to those capable of being crossed with other types, hence such introduction is not possible within plants of the same type. Also undesirable forms of the endophyte primer (mer) are introduced into later generations, so this technique does not necessarily give useful plants.

Artificial inoculation on the other hand is limited to perennial rye grass due to problems in searching for endophytes and cultivation systems, and it has never been applied to other useful grasses. In callus inoculation, it is essential to develop a regenerating system of the plant into which the endophyte is to be introduced. Moreover, inoculation conditions had not been developed to increase the rate of infection.

At present, useful endophytes have been found only in perennial rye grass, tall fescue and meadow fescue which constitutes a major limitation to their introduction. In particular, these endophytes are foreign types, and no endophytes derived from foreign plants had yet been found that were adapted to Japanese environmental conditions.

OBJECT AND SUMMARY OF THE INVENTION

It is therefore an object of the invention to provide grasses obtained by artificially introducing an endophyte into grasses not containing an endophyte, in particular an endophyte which produces an insect resisting indole alkaloid, and a method of artificially introducing such an endophyte into these grasses.

It is therefore a further object of the invention to provide bluegrasses obtained by artificially introducing an endophyte, and a method of artificially introducing such an endophyte into bluegrasses which are originally uninfected by endophytes.

This invention relates to grasses obtained by artificially introducing an endophyte into plants not containing filamentous endophytic fungi, i.e. plants not infected with an endophyte, and/or into infected plants from which endophytes have been removed. In the context of this invention, the endophyte which is artificially introduced into the grasses is an endophytic fungi that produces an insect resistant indole alkaloid. This endophyte may also be able to confer disease resistance or resistance to drought and other environmental conditions, or promote growth.

These endophytes are discovered by looking for endophytes that live in plants growing in nature, subjecting them at least to an insect resistance test, and artificially introducing those endophytes confirmed by the test to have such resistance. In nature, such endophytes are known to occur in Cyperaceae and Juncaceae.

The endophytes found and cultivated by the inventors are Acremonium sp. Po-001, Acremonium sp. M-004 or Acremonium sp. M-002 (FERM P-14798, FERM P-14799, FERM P-14800 deposited at the National Institute of Bioscience and Human Technology). All of these endophytes produce insect-resistant alkaloids and can be introduced into grasses.

The plants into which these endophytes are introduced may be any of the useful grasses belonging to the genuses Agropyron, Agrostis, Andropogon, Anthoxanthum, Arrhenatherum, Avena, Brachypodium, Bromus, Chloris, Cynodon, Dactylis, Elymus, Eragrostis, Glyceria, Hierochloe, Hordeum, Oryza, Panicum, Paspalum, Phalaris, Phleum, Poa, Setaria, Sorghum, Triticum, Zea and Zoysia. In other words, this invention relates to grasses belonging to these genuses into which endophytes are artificially introduced. In the context of this invention, this also includes future generations of grasses.

When the grass into which such an endophyte is to be introduced already contains such an endophyte, the endophyte is removed, and the endophyte producing an insect-resisting indole alkaloid is then introduced.

The method by which endophytic fungi, i.e. endophytes, are introduced into grasses, will now be described. An endophyte occurring in nature is isolated and artificially cultivated, and a grass is artificially inoculated with the cultivated endophyte. The endophyte is then introduced into the grass by infecting the grass with the inoculated endophyte.

In this inoculation step, conidiospores are particularly useful, and the aforesaid endophytes deposited at the National Institute of Bioscience and Human Technology may be used to inoculate the grass. Further, the number of types of endophyte introduced into the grass is not necessarily limited to one, it being possible to introduce two or more.

This invention further relates to a grass which is a bluegrasses obtained by artificially introducing an endophytic filamentous fungus i.e. an endophyte, into bluegrasses not originally infected with an endophyte. In the context of this invention, the term bluegrass refers to a member of the grass family, and to a plant which belongs to the genus Poa under Poaea which is a part of Pooideae. Typical examples of such grasses include Kentucky blue grass, Canada blue grass, rough meadow grass, bulbous meadow grass, alpine meadow grass, wavy meadow grass, wood meadow grass, Balforth meadow grass, swamp meadow grass, broad leaf meadow grass, narrow leaf meadow grass, smooth meadow grass, spreading meadow grass and flattened meadow grass.

To introduce endophytes into these bluegrasses, a search is made to discover endophytes living in plants growing in nature. The endophytes are isolated from the plants, and an artificial culture of them is made which is then introduced. Plants occurring in nature on which endophytes are known to live include Cyperaceae and Juncaceae.

The following endophytes were found and cultivated by the inventors, and may be used for the present purpose.

Acremonium sp. Po-001 (FERM P-14798 deposited at the National Institute of Bioscience and Human Technology)

Acremonium sp. Po-023 (FERM P-15029 deposited at the National Institute of Bioscience and Human Technology)

Epichloe sp. Po-048 (FERM P-15030 deposited at the National Institute of Bioscience and Human Technology)

The bluegrasses into which endophytes are introduced also include later generations of grasses.

The method by which endophytic fungi, i.e. endophytes, are introduced into bluegrasses, will now be described. An endophyte occurring in nature is isolated and artificially cultivated, and the bluegrass is inoculated with the endophyte. The endophyte is then introduced into the bluegrass by infecting the grass with the inoculated endophyte.

In this inoculation step, conidiospores, or any of the aforesaid endophytes deposited at the National Institute of Bioscience and Human Technology, may be used to inoculate the grass. Further, the number of types of endophyte introduced in the grass is not necessarily limited to one, it being possible to introduce two or more.

The method of introducing endophytes will now be described in still more detail.

Stage 1 Presence or absence of endophyte, and isolation of same (1) Detection of endophyte infection A leaf with its sheath was removed from a plant collected in a search, the epidermis was peeled and stained with aniline blue, and any endophyte in the tissue was detected by examination with an optical microscope.

(2) Endophyte isolation and culture

After sterilizing plant sections confirmed to contain endophyte, the endophyte was transplanted to an endophyte isolation culture and cultured for several months.

(3) Endophyte classification

Isolated endophyte was classified according to the host, or cultured by varying environmental conditions using the flat plate culture method and classified according to its morphology. Alternatively, a liquid culture was performed and the endophyte was classified according to its morphology, a slide culture was performed and the endophyte was classified according to its morphology, or a classification was made at the DNA level using the PCR method.

Stage 2 Alkaloid analysis

Alkaloid produced either by the fungus alone or when living on the plant was analyzed and examined in particular for insect resistance. Analysis for disease resistance, environmental stress resistance and growth enhancement may be made at the same time.

Stage 3 Introduction of endophyte

The isolated endophyte was artificially introduced into the desired or target grass. When the target grass already contains endophyte, this must first be eliminated. The endophyte may be introduced by directly inoculating the plant with it, alternatively non-differentiated cells such as callus can be inoculated and the plant is regenerated from the callus. An appropriate method should be chosen according to the type of plant in which it is desired to introduce the endophyte.

Stage 4 Confirmation of endophyte presence

An explant from a plant into which endophyte has been introduced is stained with a dye solution, observed with an optical microscope, and the presence of the endophyte or infection by it is detected using the enzyme immunoassay method.

Stage 5 Examination of endophyte and plants into which endophyte has been introduced (1) Resistance to pathogens An antagonistic culture was performed by the flat plate culture method, and resistance to pathogenic fungi was examined in vitro.

(2) Resistance to pests

Using plants into which endophyte had been introduced and plants either not containing endophyte or from which endophyte had been eliminated, larvae of pests were grown and damage due to them was compared. A survey of pest damage occurring in the natural environment was also carried out.

(3) Resistance to disease

Using plants into which endophyte had been introduced and plants either not containing endophyte or from which endophyte had been eliminated, resistance to disease was compared by inoculating the two types of plants with pathogenic fungi and examining the extent of disease. A survey of damage due to disease in the natural environment was also carried out.

(4) Resistance to environmental stress

Using plants into which endophyte had been introduced and plants either not containing endophyte or from which endophyte had been eliminated, environmental conditions were artificially altered, and the resistance of plants to drought and other environmental stress was compared.

(5) Resistance to eelworms

Using plants into which endophyte had been introduced and plants either not containing endophyte or from which endophyte had been eliminated, the extent of damage due to eelworms was compared.

(6) Growth

Using plants into which endophyte had been introduced and plants either not containing endophyte or from which endophyte had been eliminated, the difference in growth was measured under identical environmental conditions.

(7) Tests with later generations of plants

Seeds containing endophyte were collected, germinated, and after confirming that the endophyte was present, the aforesaid tests were performed.

As stated hereintofore, this invention relates to grasses obtained by artificially introducing filamentous endophytic fungi or endophytes, in particular endophytes which produce an insect resisting indole alkaloid, into grasses which do not contain such an endophyte, and to a method of artificially introducing such endophytes into these grasses.

According to this invention, therefore, it is possible to confer at least insect resistance on grasses by artificially introducing an endophyte which produces an indole alkaloid having such resistance into these grasses. By further conferring disease resistance and environmental stress resistance due to this artificial endophyte infection, the characteristics of the grass are improved and/or a useful grass having excellent characteristics can be provided.

As stated hereintofore, another invention relates to a glass which is a bluegrasses obtained by artificially introducing filamentous endophytic fungi or endophytes, in particular endophytes which produce an insect resisting indole alkaloid, into bluegrasses not containing such endophytes, and to a method of artificially introducing these endophytes into bluegrasses.

According to another invention, therefore, it is possible to confer at least insect resistance on bluegrasses by artificially introducing such an endophyte into bluegrasses. The characteristics of the bluegrasses are thereby improved, and useful bluegrasses having excellent characteristics can be provided.

The above and other objects, features and advantages of this invention will be apparent from the following examples which are to be read in connection with photographic drawings.

EXAMPLE I (1) Detection of endophyte

Seeds of the wild grasses Agrostis, Poa and Phleum pratense were sown, and the endophyte detected from the plants produced after 120 days germination.

The epidermis of leaves and leaf sheaths of these plants were removed, and the presence or absence of endophyte in the tissue was confirmed by an optical microscope examination. This confirmation was performed as follows. 5 ml of lactic acid, 10 ml of glycerine, 5 ml of water and several drops of an aqueous solution of aniline blue were placed on a glass slide. The leaf sheath was peeled with forceps, and the underside epidermis was peeled away toward the leaf vein. The peeled epidermis was placed on a glass slide, covered with a cover glass, boiled in the flame of a gas burner and the tissue was observed with an optical microscope. When the endophyte is present the mycelium appears blue, so it is possible to detect the endophyte by this procedure.

Figure 1:
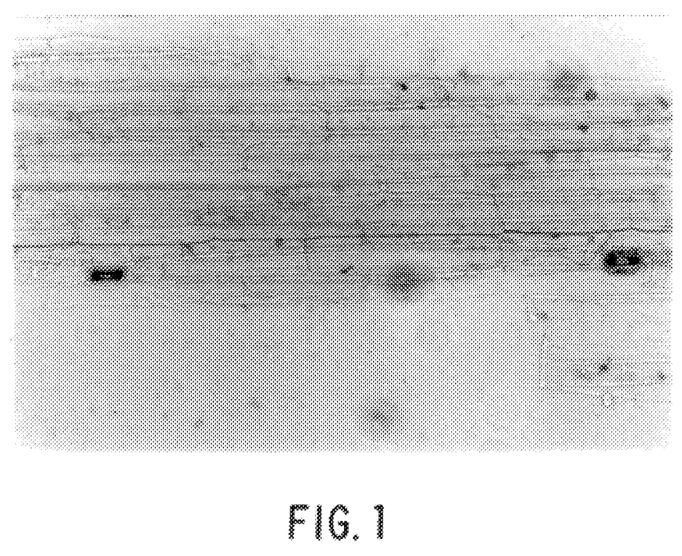
FIG. 1 is a microphotograph of an endophyte living in a plant obtained by dyeing the endophyte.

FIG. 1 is a photographic enlargement obtained by an optical microscope of Acremonium sp. M-004 (deposit number FERM P-14799), an endophyte living on the genus Agrostis.

(2) Isolation of endophyte The endophyte in the aforesaid section (1) was isolated from the genuses Agrostis, Poa and *Phleum pratense* in which it was detected.

To isolate the endophyte from the plant, the leaf and leaf sheath were washed with water, immersed in a 70% aqueous solution of ethanol for 10 seconds, immersed in a 2.5% aqueous solution of sodium hypochlorite for 10 minutes, washed 3 times with sterile water, transferred to an endophyte isolation culture, and cultivated in the dark at 25° C.

The isolation culture was prepared by sterilizing PDA (potato dextrose agar) adjusted to pH 5.6 at 121° C. for 15 minutes, adding 100 mg/l kanamycin sulfate if necessary, and pipetting 20 ml portions into plastic Petri dishes of diameter 9 cm.

After approx. 3–8 weeks, the mycelium was isolated from an explant, and the colonies were removed by a cork borer of diameter 5 mm, transferred to a PDA culture and grown.

(3) Classification and identification of endophytes by using the flat plate culture method The mycelium transplanted to the PDA culture was grown in the dark at 25° C., and the colonies formed were examined. As a result, the endophytes isolated from the genus Agrostis were classified into 3 types according to the colonies formed. The first type (001) was characterized by cottony dome-shaped colonies having a white surface. The second type (002) was characterized by cottony colonies with a brown, clay-like center and white outer circumference which grew while spreading a pale white substance through the culture. The third type (004) was characterized by white, cottony colonies which were somewhat dome-shaped at the beginning, and then flattened out.

From a DNA analysis using the PCR method of these types, it was determined that 001 and 004 were identical, two types of endophytes being isolated from the genus Agrostis.

From the genus Poa, one type of endophyte was isolated. The colonies on the culture were cottony and yellowish white.

From the genus Phleum pratense, one type of endophyte, *Epichloe typhina* (referred to hereafter as *E. typhina*) was isolated. The colonies had a white surface, some of the mycelia were bundled together, and grew out from the center to form an "S" shape. This endophyte grew best of all the endophytes.

002, 004 isolated from the genus Agrostis, and the endophyte isolated from the genus Poa, were deposited at the National Institute of Bioscience and Human Technology which belongs to the Agency of Industrial Sience and Technology. The description and deposition numbers of these endophytes are as follows.

Endophyte 002 isolated from genus Agrostis: Acremonium sp. M-002 FERM P-14800
Endophyte 004 isolated from genus Agrostis: Acremonium sp. M-004 FERM P-14799
Endophyte isolated from genus Poa: Acremonium sp. Po-001 FERM P-14798

(4) Growth differences due to temperature

After growing the aforesaid endophytes deposited at the National Institute of Bioscience and Human Technology and *E. typhina* on PDA culture for 2 months at 25° C. in the dark, colonies were removed with a cork borer of diameter 5 mm, transferred to a PDA culture and CMA (corn meal agar) culture, and grown for 2 months at temperatures of 10° C., 15° C., 20° C., 25° C. and 30° C. respectively so as to investigate the change in the colonies according to temperature difference. All these tests were conducted in the dark.

As a result, all endophytes were found to grow best at 25° C., and showed relatively good growth at the high temperature of 30° C. At 5° C. and below, practically no colonies were formed.

(5) Liquid culture

After growing FERM P-14798, FERM P-14799, FERM P-14800 and *E. typhina* for 2 months on a PDA culture at 25° C. in the dark, colonies were removed by a cork borer of diameter 5 mm, 100 ml of PD (potato dextrose) broth was placed in each of 300 ml flasks with shaking, and each colony was introduced in each flask by an apparatus which had been sterilized at 121° C. for 15 minutes, and shaking was performed at 25° C. with a back and forth motion at 150 r.p.m.

As a result, all the fungi spread throughout all the flasks in one month. 1 ml was then removed from each flask, transferred to a fresh PD culture, and grown under the same conditions. FERM P-14800 formed conidiospores from the 4th day of culture, and their amount reached a peak at 5–10 days.

(6) State of mycelium by slide culture

A PDA culture of thickness 2–3 mm was mounted on a glass slide, mycelium was grown on the culture, and the morphology of the mycelium and conidiospores were examined. This culture was performed at 25° C. in the dark.

Figure 2:
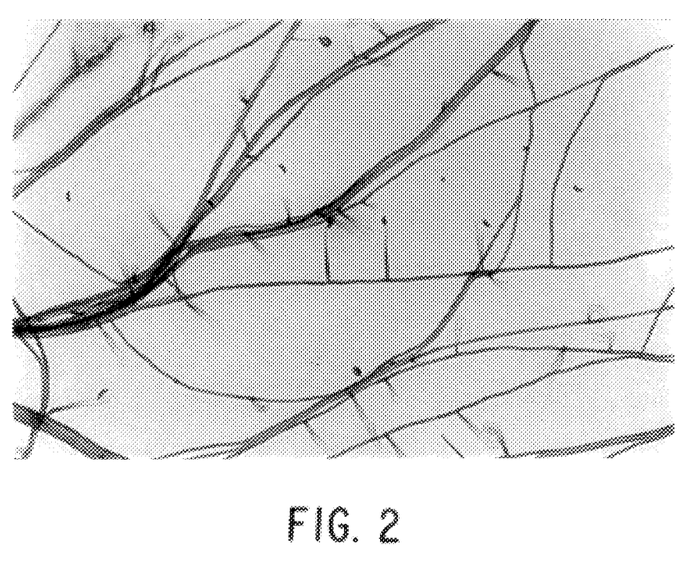
FIG. 2 is a microphotograph of mycelium grown on a PDA culture.

As a result, it was found that the mycelium of FERM P-14798, PERM P-14799 and *E. typhina* grew effectively in linear filaments often forming bundles. FIG. 2 is a microphotograph of the mycelium of FERM P-14799 grown on PDA culture. In contrast, the mycelium of the endophyte FERM P-14800 grew with strong undulations, in an "S" shape, again often forming bundles.

All mycelia were colorless, and partitions of width 1–2 $\mu$m were observed throughout. All endophytes were easily able to form conidiospores.

Figure 3:
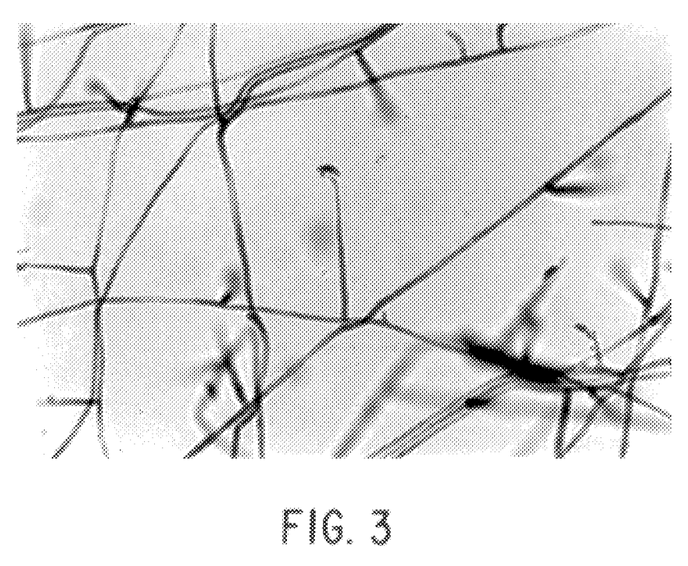
FIG. 3 is a microphotograph of conidiospores formed on a PDA culture.

The conidiospores were formed at the ends of single phialides emerging from the ends or sides of the mycelium, and most were single conidiospores. FIG. 3 is a microphotograph of mycelium conidiospores of FERM P-14799 formed on a PDA culture.

All conidiospores were colorless, and monocellular. Although the conidiospores were somewhat elliptical in the case of *E. typhina,* most were kidney-shaped and 3–8×1–3 $\mu$m in size. The phialides formed were all cylindrical tapering towards the ends, and separated from the mycelium by partitions.

(7) Elimination of endophyte by heat treatment

The endophyte was eliminated from seeds in which it was present by heat treatment as follows.

1 ml of water was introduced into a 1 ml Eppendorf tube, and kept at 57° C. by a dry block. Ten seeds were placed in each tube, and heated at 57° C. for 5 minutes. After treatment, the seeds were transferred immediately to water and cooled.

After treating with sulfuric acid at 35° C. for 3 hours, if necessary, the seeds were immersed in a 70% aqueous ethanol solution for 10 seconds, immersed in 2.5% aqueous sodium hypochlorite solution, washed 3 times in sterile water and dried in a current of air.

(8) Detection of endophyte by enzyme immunoassay (ELISA)

The endophyte was detected in seeds and explants by the following method.

Buffer solution was added to 0.5 g raw weight of an explant, and the mixture was crushed in a mortar so as to obtain an extract. 50 $\mu$l of this extract was placed in a well in a microplate, and adsorbed at room temperature for 30 minutes. Uncombined antigen was washed out.

The well was filled with blocking solution (3% skimmed milk solution) and washed 30 minutes later. Anti-endophyte rabbit antiserum (primary antibody) was added to the well, and reacted at room temperature for 60 minutes. Uncombined antibody was washed out.

Diluted secondary antibody (antirabbit IgG, goat labelled with alkali phosphatase) was added to the well, and reacted at room temperature for 60 minutes. Uncombined antibody was washed out. A basic solution was then added to the well so as to cause an alkali phosphatase reaction. The reaction was stopped by 0.5N NaOH, and the degree of light absorption at 405 nm was measured. As a result, seeds and plants containing the endophyte gave a color reaction, but no such reaction was observed in seeds and plants not containing the endophyte.

(9) Artificial inoculation using plants

Of the endophytes that were isolated, specimen plants were artificially inoculated using FERM P-14798, FERM P-14799 and FERM P-14800. In the case of seeds of plants already containing an endophyte, the endophyte was eliminated from the seeds by the method of (7), and used after some had been examined by the method of (8).

The specimen plants used here were as follows:
Genus Agrostis: Agrostis sp., *A. stolonifera, A. gigantia, A. tenuis*
Genus Poa: Poa sp., *P. pratense*

The aforesaid endophytes were first grown according to the method of (5), transferred to a fresh PD culture, and grown under the same conditions for 5–12 days. Inoculation was performed by germinating seeds on an MS (Murashige-Skoog) base culture obtained by adding 3.0% sucrose and 0.7% gellan gum to an MS culture. After 1–2 weeks, plants or runners and shoots in the case of long-term cultures were cut off with a knife, and 1 ml of a liquid culture of the mycelium prepared as in (5) was dripped in.

After several weeks culture in the dark at 25° C. and 30° C., the plants were placed under illumination for 16 hours, or alternatively they were grown under illumination for 16 hours from the start. Plants which had turned green were transferred to a culture of the same composition, and grown for one month.

After applying the methods described in (1) and (8) to confirm the presence of endophyte, it was found that FERM P-14798, FERM P-14799 and FERM P-14800 had all been introduced into the plants.

The infection rate was clearly higher at 30° C. than at 25° C.

(10) Artificial inoculation using callus

Callus was induced in plants of the genus Agrostis. For this purpose, Agrostis sp. and *A. stolonifera* were used, and a callus induction culture was prepared by adding 2.0 mg/l of PIC (picolam) and 0.2 mg/l of BAP (6-benzylaminopurine) to an MS base culture.

Seedlings obtained immediately after germination on an MS culture were transplanted to callus induction cultures, and cultured for 2 months in the dark at 25° C. so as to obtain callus which had differentiating ability. In the case of Agrostis sp., seeds from which prior endophyte infection had been eliminated by the method of (7) were used.

Artificial inoculation with FERM P-14799 and FERM P-14800 was performed using callus from Agrostis sp. and *A. stolonifera*. Calluses were induced on the aforesaid induction culture, and the callus obtained was transferred to an MS base culture without the addition of plant hormone.

Immediately after transferring, the callus was cut with a knife, and 50 µl of mycelium per callus, grown as in (5), was dripped in. In the case of Agrostis sp., both of the endophytes FERM P-14799 and FERM P-14800 were introduced.

The callus was cultured for several weeks in the dark at 25° C. and 30° C., then placed under illumination for 16 hours, or alternatively it was placed under illumination for 16 hours from the start. The regenerated plant was then transferred to a fresh MS culture and grown for one month. When an examination was made for presence of endophyte according to the methods described in (1) and (8), the mycelium showed a coloration and gave a color reaction in the case of both FERM P-14799 and FERM P-14800. This confirmed that endophyte had been introduced.

The infection rate was higher at 30° C. than at 25° C., there clearly being a significant difference. The infection rate was also higher than in the method of direct introduction into the plant described in (9).

Any endophyte adhering to the surface of the plants obtained by introducing FERM P-14799 and FERM P-14800 was completely removed, and using the same method as that described in (2), both FERM P-14799 and FERM P-14800 were isolated from the same explant. This shows that it is possible to introduce a plurality of endophytes.

(11) Mass production of conidiospores

Conidiospores were mass produced using FERM P-14800 for which the formation of conidiospores had been confirmed in a liquid culture. FERM P-14800 was cultured by the same method as that of (5), and transferred to a fresh PD culture. 20 ml of culture liquid was removed after 5–10 days when the ability to form conidiospores is at a peak, and unwanted mycelium was removed by two superposed 20 µm meshes. 10 ml of the filtrate was placed in a centrifuge tube, and centrifugation was performed at 1000 r.p.m. for 10 minutes. After centrifuging, the supernatant liquid was discarded and 1 ml of PD culture was added so as to obtain a suspension of conidiospores.

(12) Inoculation method using conidiospores

Agrostis sp. and *A. stolonifera* were artificially inoculated with a conidiospore suspension of FERM P-14800 using the callus inoculation method described in (11). After examining the plants obtained by the methods described in (1) and (8), many plants were found to contain the endophyte, and there was a significant difference compared to the inoculation method of (10) using the mycelium.

(13) Antagonistic culture

An antagonistic culture was performed under flat plate culture conditions using FERM P-14799 and FERM P-14800. The pathogenic fungi studied were *Rhizoctonia solani, Gaeumannomyces graminis, Sclerotinia homeocarpa,* Curvularia sp. and Helminthosporium sp.

To perform the antagonistic culture, a PDA culture was placed in a sterile Petri dish of diameter 9 cm, and one endophyte colony removed by a cork borer of diameter 5 mm was placed in the center of the dish. After one month culture, a colony of pathogenic fungi was placed at a radius of 3 cm from the center of the endophyte colony, and the culture was grown for 3 weeks in the dark at 25° C.

As a result, both FERM P-14799 and FERM P-14800 temporarily interfered the elongation of all the pathogenic fungi, and FERM P-14800 showed particular resistance to *Rhizoctonia solani* and Curvularia sp.

(14) Analysis of alkaloids from plants

An alkaloid analysis was performed using a specimen MI-14800 obtained by introducing FERM P-14800 endophyte into Agrostis sp., and a specimen MF of Agrostis sp. from which the endophyte had been eliminated.

After freeze drying the leaves and leaf sheaths of these specimens, a 100 mg sample was placed in a mortar and crushed, 1.5 ml each of methanol and chloroform were added and blended, and the liquid was recovered in a centrifuge sedimentation tube. The mixture was carefully blended for 30 minutes at 18° C., 3 ml each of n-hexane and water were added and the mixture was stirred for 30 minutes. After centrifuging at 2000 r.p.m. for 10 minutes, an organic layer and an aqueous layer were separated (pipetted off).

3 ml of the aqueous layer was purified on a Biorad Ag2×8 and an Analytichem Bond Elut CBA column, and after concentration, 100 μl of 80% methanol was added. 20 μl of each sample was dripped onto a thin layer plate coated with Merck silica gel 60, and using a chloroform, methanol, acetic acid and water mixture in the ratio 20:10:1:1 as developer, an analysis was performed by TLC (thin layer plate chromatography).

A 200 μl sample of the organic layer fraction was placed in a 1 ml Eppendorf tube, and after completely evaporating off the solvent in a rotary evaporator, the pellets were taken up in 200 μl of chloroform. 150 μl of 2% tartaric acid was then added, and the mixture was blended for 10–15 minutes. Following this, it was centrifuged at 10000 r.p.m. for 3 minutes, and pH was adjusted to 9–10 by 4M NaOH. 200 μl of chloroform was added and the mixture was blended for 10–15 minutes, following which it was centrifuged at 1000 r.p.m. for 3 minutes.

The chloroform layer was aspirated (pipetted off), and after concentration, 20 μl of each sample was added to a thin layer plate coated with Merck silica gel 60. Using chloroform and methanol in the ratio 9:1 as developer, an analysis was performed by TLC.

After developing, the water layer and organic layer extracts were confirmed by UV, and the color reaction and Rf values were measured using the Ehrlich reagent (solution of 1.0 g p-dimethylbenzaldehyde in 96% ethanol) and the Dragendorff reagent.

The aqueous layer extract of MI-14800 showed a reaction under UV at Rf 0.43. Using the Ehrlich reagent, a bluish purple spot was found, while using the Dragendorff reagent, an orange spot was found at the same position. This color reaction and Rf value confirmed the presence of an indole alkaloid.

The organic layer extract gave four spots under UV with Rf values of 0.30, 0.37, 0.52 and 0.58 respectively. When the Ehrlich reagent was used, bluish purple spots were obtained whereas, using the Dragendorff reagent, orange spots were found at the same positions. These color reactions and Rf values confirmed the presence of indole alkaloids. In the case of MF which did not contain endophyte, neither the aqueous layer or organic layer gave any color reaction with Ehrlich reagent or Dragendorff reagent, thus confirming that these indole alkaloids were produced only by the endophyte alone or by the endophyte-plant combination.

(15) Resistance to webworm

Resistance to webworm was compared using plants containing endophyte and plants not containing endophyte. The plants containing endophyte which were used in this test were MI-14800 i.e. FERM P-14800 introduced into Agrostis sp., MI-14799 i.e. FERM P-14799 introduced into Agrostis sp., MW derived from Agrostis sp. seeds, PCI-14800 i.e. FERM P-14800 introduced into *Agrostis stolonifera,* and PCI-14799 i.e. FERM P-14799 introduced into *Agrostis stolonifera.*

Plants not containing endophyte which were used in this test were MF i.e. Agrostis sp. from which endophyte had been eliminated, and PC derived from *Agrostis stolonifera* seeds from which endophyte had been eliminated.

Specimens were prepared as follows. Seeds of MW and PC were immersed in a 70% aqueous solution of ethanol for 10 seconds, immersed in a 2.5% aqueous solution of sodium hypochlorite for 10 minutes, washed 3 times with sterile water, dried in a current of air and transferred to an MS base culture. After germinating, the seedlings were cultivated for one month.

MI-14799, MI-14800 and PCI-14799, PCI-14800 prepared as described in (10) were transferred to an MS base culture and cultivated for one month.

For MF, after eliminating endophyte by the method described in (7), seeds were immersed in a 70% aqueous solution of ethanol for 10 seconds, immersed in a 2.5% aqueous solution of sodium hypochlorite for 10 minutes, washed 3 times with sterile water, dried in a current of air and transferred to an MS base culture. Seedlings cultivated one month after germination were used. All the specimens used were examined by the methods described in (1) and (8).

20 g of culture medium and 5 ml of water were placed in 6×6×10 cm plant boxes, and ten sterilized specimens were planted in each box. These were cultivated for one week at 25° C. under 16 hour daylight conditions to give specimen 2.

Webworm eggs were immersed in 70% ethanol for 10 seconds, washed with sterile water 3 times and dried in a current of air. Approximately 200 eggs were then distributed in each of the plant boxes containing sample 2.

The eggs hatched in one week and insect damage began. Initially, webworm larvae damaged all of specimen 2, however in the case of MI-14799, MI-14800, PCI-14799, PC-14800 and MW the damage stopped. Whereas MF and PC were completely damaged in 3–4 days, MI-14799, MI-14800, PCI-14799, PCI-14800 and MF all suffered only initial damage. The same effect was moreover obtained for MW, MI-14799 and MI-14800.

Instead of the aforesaid test, the following insect resistance test may be performed. In this insect resistance test, webworm eggs were surface sterilized, approx. 200 were transferred to a Petri dish of diameter 9 cm, and hatched in an incubator at 25° C. Immediately after hatching, a moist filter paper was placed in the dish, leaf sections cut to approx. 5 mm square size were introduced, and the presence or absence of insect damage was investigated after 24 hours and 48 hours respectively.

It was found that after 24 hours, at least 50% of the leaves of the plant not infected by endophyte was damaged by insects, and after 48 hours, all the leaves of uninfected plants were damaged. On the other hand, leaves of plants infected by endophyte were still undamaged even after 48 hours.

(16) Resistance to Japanese lawn grass cutworms

Two cutworm larvae were placed in each plant box, and insect damage was examined using specimens prepared according to the same method as that described in (15).

The larvae immediately began to attack the plants, however in MI-14799, MI-14800, PCI-14799, PC-14800 and MW which contained endophyte, the damage stopped when it had reached approx. ⅓. Whereas MF and PC were completely damaged in 2 days, MI-14799, MI-14800, PCI-14799, PCI-14800 and MW all suffered damage to the extent of only about ⅓.

(17) Resistance to *Rhizoctonia solani*

A 5 mm square was cut from a Rhizoctonia solani colony which had been cultured for 2 weeks on a PDA culture. Using the same specimens as in (15), 5 specimens were buried in earth in each plant box, and cultivated at 28° C. for one month under 16 hour daylight conditions.

In the case of PC and MF which did not contain endophyte, leaf rot began in the first week after inoculation, and the plants had completely withered after 3 weeks. On the other hand, in the case of MI-14799, MI-14800, PCI-14799, PC-14800 and MW which contained the endophyte, withering of leaves began only 2 weeks later. Although mycelium like a spider's web was observed on the leaf surface, the progression of the disease was slow and the plant did not wither completely. This clearly showed a significant difference of resistance.

(18) Resistance to Curvularia sp.

Conidiospores formed on the surface were removed with a needle from colonies of Curvularia sp. that had been cultivated for one month on a PDA culture. The spores were suspended in a sterile liquid and adjusted to a concentration of 5000–10000/ml. Using the same specimens as in (15), the entire surface of the plants was sprayed or coated with this suspension, and the plants cultivated at 28° C. for one month under 16 hour daylight conditions.

After the fourth day of culture, the tips of the leaves of all the plants began to develop Curvularia spot. However, whereas in PC and MF, Curvularia spot continued to progress in approx. ¾ of all the leaves, in MI.-14799 and PCI-14799 containing endophyte the disease stopped at about ⅓, and in MI-14800, PCI-14800 and MW, only slight blotches were formed.

(19) Resistance to drought

Aluminum foil was laid in transparent pots of diameter 12 cm and height 10 cm, the pots were packed to a height of 3 cm with stones of size 1 cm, and river sand was laid on top to a height of 7 cm. One group from specimen 2 prepared in (15) was planted in each pot, and the plants grown at 25° C. under 16 hours illumination.

Cultivation was continued for approx. 2 weeks while supplying sufficient water for growth. After verifying that the roots were properly anchored in the soil, the plant was monitored until water had drained off, and when it was visually confirmed that there was no more water, 100 ml of water was added. This procedure was repeated for one month.

In the case of PC and MF which did not contain endophyte, the plants clearly started to droop when the initial water had been used up. After the first watering not much recovery was observed, and after the second watering the plant had effectively died.

In the case of MI-14799, MI-14800, PCI-14799, PC-14800 and MW which contained endophyte, however, the leaves rolled up into a needle shape which is characteristic of endope-infected plants when the initial water had become less, and the plants were still green after one month. This clearly showed a significant difference with respect to drought.

(20) Greenhouse pot test

Stones of size 1 cm were packed to a height of approx. 3 cm in pots of diameter 12 cm and height 10 cm, and river sand was laid on top to a height of approx. 7 cm. One group of specimen 2 prepared in (15) was planted in each pot, the plants were transferred to a greenhouse, and an acclimatization culture was performed. The culture conditions were watering every morning and supplying Hyponex diluted 500 times once a month in the same way. After 3 months, the plant was removed from the pot, soil adhering to the roots was washed off, then the stem hight above ground, proliferation of roots, plant weight and occurrence of disease were measured.

In Agrostis sp., MI-14799, MI-14800 and MW which contained the endophyte showed healthier stems, higher root proliferation and plant weight, in comparison to MF which did not contain the endophyte. The shoots were also proliferant and there was a clear difference with regard to growth.

In *A. stolonifera,* PCI-14799 and PCI-14800 which contained the endophyte showed healthier stems, higher root proliferation and plant weight, in comparison to PC which did not contain the endophyte. The growth of runners was proliferant, and there was clearly not much withering due to Fusarium spp. or withering disease due to Curvularia spp. and Drechslera spp.

(21) Field test without mowing

The same specimens as those described in (15) were transplanted to a field, and a growth test was performed. Plants were planted into 1×1 m areas five at a time, and cultivated during the 6 month period from April to September without mowing.

As a result, Agrostis sp., *A. stolonifera,* MF and PC in which the endophyte was not present were severely affected by rust disease, however in the case of MI-14800, PCI-14799, PCI-14800 and MW which did contain endophyte, disease did not spread through all of the plants although a few summer spores were observed. Also whereas with MF and PC a large number of nematodes were collected from bases of parts with poor leaf color, only a small number of nematodes were observed with MI-14799, MI-14800, PCI-14799, PCI-14800 and MW.

(22) Field test by turfing

Similar plants to those described in (15) were used. Soil comprising a blend of sand and permiculate was evenly placed in a 30×60 growing box for grass to a height of 2 cm, and the plants was introduced so that they were packed closely together for each specimen. Mowing was regularly performed when the plants reached a height of 10 mm, and cultivation was continued at room temperature for 3 months.

After 3 months, the shoots in the box were transplanted to a field and a growth test was performed. Five sheets were planted in 1×1 m areas, mowing and rolling were performed, cultivation was continued for the 6 month period from April to September and a growth test was performed.

As a result, in the case of *A. stolonifera*, with PC which did not contain endophyte, a large amount of take all patch due to *Gaeumannomyces graminis* occurred from May to June, while there was brown patch due to *Rhizoctonia solani* and Dallas spot due to *Sclerotinia homoeocarpa* from July to August. On the other hand, in the case of PCI-14799 and PCI-14800 which did contain endophyte, there was only a small initial patch of approx. 20 cm due to these diseases, and the plant recovered quickly. Regarding Dallas spot, a significant difference was noted to the extent that practically no spots were seen.

In the case of PC which not contain endophyte, a considerable amount of damage was observed on the roots due to the larvae of gold bug, whereas in the case of PCI-14799 and PCI-14800, no disease due to these larvae was seen on the roots in the turf.

In Agrostis sp., with MF which did not contain endophyte, leaf rot due to Rhizoctonia sp., leaf withering due to Curvularia spp. and Helminthosporium spp., pythium blight due to Pythium spp. and pythium blight occurred from July to September. With MI-14799, MI-14800 and MW which contained endophyte, although small patches were observed at first, these disappeared within a short period of time. There was thus a significant difference with regard to the occurrence of and recovery from disease.

From mid-July to mid-September, damage was observed due to natural proliferation of webworm. At sunset, a large number of the moths flew in to lay eggs on the turf. At the 3rd–4th day after the peak of this invasion, in PC and MF to which endophyte was not present, damage began to be observed due to webworm larvae, and after one week approx. ⅔ of the turf had been ravaged.

In contrast, in the case of MI-14799, MI-14800, PCI-14799, PCI-14800 and MW which were infected with endophyte, although eggs were observed on the leaves immediately after the moths had laid them, no further damage was observed at all. A significant difference was therefore clearly seen with regard to the damage caused by webworm.

(23) Insect resistance using later generations of plants into which endophyte was introduced Seeds were collected from MI-14800 and PCI-14800 which had been artificially inoculated with endophyte. After germination, related groups containing endophyte were selected by the methods described in (1) and (8), and resistance to webworm was examined by the same method as described in (15). MF and PC were used as a comparison group.

As a result, although all plants were initially damaged by webworm, the damage was halted in plants obtained from the seeds of MI-14800 and PCI-14800. Whereas MF and PC were completely ravaged after 3–4 days, plants obtained from the seeds of MI-14800 and PCI-14800 had only initial damage and the same result as that of (15) was obtained. This confirmed that the results due to the presence of endophytes are passed on to future generations via seed.

EXAMPLE II (1) Detection of endphyte

Using the following method, endophyte was detected in plants of the genus Poa which naturally lives as wild grasses.

The epidermis of leaves and leaf sheaths of these plants were removed, and the presence or absence of endophyte in the tissue was confirmed examination with an optical microscope. This confirmation was performed as follows. 5 ml of lactic acid, 10 ml of glycerine, 5 ml of water and 0.02 g of an aqueous solution of aniline blue were placed on a glass slide. The leaf sheath was removed with forceps, and the underside epidermis was peeled away toward the leaf vein. The peeled epidermis was placed on a glass slide, covered with a cover glass, boiled in the flame of a gas burner and the tissue was observed with an optical microscope. When the endophyte is present, the mycelium appears blue, so it is possible to detect the endophyte by this procedure.

As a result, endophytes were detected in 3 plants belonging to the genus Poa. From the life cycle of the fungus, two types were *Acremonium endophytes* with only asexual generation which did not move outside the plant, the remaining type being an *Epichloe endophyte* with sexual generation and which forms stroma or chokes during the earing period.

(2) Isolation of endophyte

The endophyte was separated from the 3 plants of the genus Poa wherein endophyte was detected by the aforesaid method (1).

To isolate the endophyte from the plant, the leaf and leaf sheath were washed with water, immersed in a 70% aqueous solution of ethanol for 10 seconds, immersed in a 2.5% aqueous solution of sodium hypochlorite for 10 minutes, washed 3 times with sterile water, transferred to an endophyte isolation culture, and cultivated in the dark at 25° C.

The isolation culture was prepared by sterilizing PDA (potato dextrose agar) adjusted to pH 5.6 at 121° C. for 15 minutes, adding penicillin and streptomycin so that their respective concentrations were 100 mg/l, and pipetting 20 ml portions into plastic Petri dishes of diameter 9 cm.

After developing the culture for approx. 3–8 weeks, the mycelium was isolated from the explant, the colonies was removed by a cork borer of diameter 5 mm and transferred to the same PDA culture and grown.

(3) Classification and identification of endophytes by colonies using the flat plate culture method The mycelium transplanted to the PDA culture was grown in the dark at 25° C., and the colonies formed were examined. As a result, all the colonies on the culture were white and cottony. They grew very slowly, and in one month had reached a radius of only about 2 cm.

The 3 endophytes which had been isolated were deposited at the National Institute of Bioscience and Human Engineering which is part of the Agency of Industrial Science and Technology, their names and numbers being as follows.

Acremonium sp. Po-001 FERM P-14798
Acremonium sp. Po-023 FERM P-15029
Epichloe sp. Po-048 FERM P-15030

(4) State of mycelium by slide culture

A PDA culture of thickness 2–3 mm was mounted on a glass slide, the mycelium was grown on the culture, then the characteristics of the mycelium and formation of conidiospores were examined. This culture was performed at 25° C. in the dark.

As a result, it was found that the mycelia were completely colorless, their width was 1–2 $\mu$m, and partitions were observed in all of them. All the endophytes were easily able to form conidiospores.

The conidiospores were formed at the ends of single phialides emerging from the ends or sides of the mycelium, and most of them were single conidiospores.

All the conidiospores were colorless, and were monocellular. Most of them were kidney-shaped and $3-8 \times 1-3$ $\mu$m in size. The phialides formed were all cylindrical tapering towards the ends, and separated from the mycelium by partitions.

(5) Analysis of plant alkaloids

An analysis of alkaloids from the host plants of FERM P-14798, FERM P-15029 and FERM P-15030 was performed by the following method.

After freeze drying the leaves and leaf sheaths of these specimens, a 100 mg sample was placed in a mortar and crushed, 1.5 ml each of methanol and chloroform were added and blended, and the liquid was recovered in a centrifuge sedimentation tube. The mixture was carefully blended at 18° C. for 30 minutes, 3 ml each of n-hexane and water were added and the mixture was stirred for 30 minutes. After centrifuging at 2000 r.p.m. for 10 minutes, an organic layer and an aqueous layer were separated (pipetted off).

3 ml of the aqueous layer was purified on a BioRad AG2×8 and an Analytichem Bond Elut CBA column, and after concentration, 100 $\mu$l of 80% methanol was added. 20 $\mu$l of each sample was dripped onto a thin layer plate coated with using Merck silica gel 60 and using a chloroform, methanol, acetic acid and water mixture in the ratio 20:10:1:1 as developer, an analysis was performed by TLC (thin layer plate chromatography).

500 $\mu$l samples of the organic layer fraction were placed in 2 ml Eppendorf tubes, and after completely evaporating the solvent off in a rotary evaporator, the product was diluted to 200 $\mu$l with chloroform. After dilution, 3 $\mu$l of each sample was dripped onto a thin layer plate coated with Merck silica gel 60, and an analysis was performed by TLC using chloroform and methanol in the ratio 9:1 as developing solvent.

After developing, the water layer and organic layer extracts were confirmed by UV, and the color reaction and Rf values were measured using the Ehrlich reagent (solution of 1.0 g p-dimethylbenzaldehyde in 96% ethanol) and nitrosonaphthol reagent.

Using the Ehrlich reagent, the aqueous layer extracts from the host plants of FERM P-14798, FERM P-15029 and FERM P-15030 gave a bluish purple spot. This color reaction and Rf value confirmed the presence of an indole alkaloid.

Using the Ehrlich reagent, the organic layer extracts from all the host plants of FERM P-14798, FERM P-15029 and FERM P-15030 gave bluish purple spots. Using nitrosonaphthol reagent, only the host plant of FERM P-15030 gave a reddish purple spot at the same position. These color reactions confirmed the presence of indole alkaloids.

(6) Liquid growth culture

After growing FERM P-14798, FERM P-15029 and P-15030 for 2 months on a PDA culture at 25° C. in the dark, colonies were removed by a cork borer of diameter 5 mm, 100 ml of PD (potato dextrose) broth was placed in each of 300 ml flasks with shaking, one colony was introduced in each flask by an apparatus which had been sterilized at 121° C. for 15 minutes, and shaking was performed at 25° C. with a back and forth motion a 150 r.p.m.

As a result, all fungi spread through the whole flask in 1 month.

(7) Artificial inoculation using plants

Kentucky bluegrass, a type of bluegrass, was artificially inoculated using the isolated endophytes FERM P-14798, FERM P-15029 and FERM P-15030.

The specimen plants used here were Kentucky bluegrasses of the strains Baron, Merion, Kenblue and Troy.

The aforesaid endophytes were first grown according to the method of (6), transferred to a fresh PD culture, and grown under the same conditions for 5–12 days. Inoculation was performed by germinating seeds on an MS (Murashige-Skoog) base culture obtained by adding 3.0% sucrose and 0.7% gellan gum to an MS culture. One week after germination, an incision was made in the plant with a knife, and 10 μl of a liquid culture of the mycelium prepared as in (6) was dripped in.

After several weeks culture in the dark at 25° C. and 30° C., the plants were placed under illumination for 16 hours, or alternatively they were grown under illumination for 16 hours from the start. Plants which had turned green were transferred to a culture of the same composition, and grown for one month.

After applying the method described in (1) to confirm the presence of endophyte, it was confirmed that FERM P-14798, FERM P-15029 and FERM P-15030 had all been introduced into the plants. The infection rate was clearly higher at 30° C. than at 25° C.

(8) Artificial inoculation using callus

Callus was induced in Kentucky bluegrass as a specimen for artificial inoculation. Various strains of Kentucky bluegrass were used to provide specimens, viz. Baron, Merion, Kenblue and Troy. A callus induction culture was prepared by adding 2.0 mg/l of PIC (picolam) and 0.2 mg/l of BAP (6-benzylaminopurine) to an MS base culture.

Seedlings obtained immediately after germinating on an MS culture were transplanted to callus induction cultures, and cultured for 2 months in the dark at 25° C. so as to obtain callus which had differentiating ability.

Artificial inoculation with FERM P-14798, FERM P-15029 and FERM P-15030 was performed using callus from Kentucky bluegrass. A callus was first induced on the aforesaid induction culture, and the callus obtained was transferred to an MS base culture without the addition of plant hormone.

After transferring, the callus was immediately cut with a knife, and 50 μl of mycelium per callus, grown as in (6), was dripped in.

The callus was cultured for several weeks in the dark at 25° C. and 30° C., then placed under illumination for 16 hours, or alternatively it was placed under illumination for 16 hours from the start. The regenerated plant was then transferred to a fresh MS culture and grown for one month. When an examination was made for presence of endophyte according to the method described in (1), it was found that FERM P-14798, FERM P-15029 and FERM P-15030 had been introduced into all strains.

FERM P-14798 and FERM P-15030 were introduced into the Baron strain of Kentucky bluegrass using the same method as described in (8). The mycelium was isolated from these plants and after cultivation, two types of fungi with slightly different colonies were isolated and detected.

When these were analyzed using the PCR method, FERM P-14798 and FERM P-15030 showed characteristic band patterns and similar patterns, thus confirming that two types of endophyte were living in Kentucky bluegrass into which two types of endophyte had been introduced.

(9) Mass production of conidiospores

Conidiospores were mass produced using FERM P-14798 for which the formation of conidiospores had been confirmed in a liquid culture. FERM P-14798 was cultured by the same method as that of (6), and transferred to a fresh PD culture. 20 ml of culture liquid was removed after 5–12 days when the ability to form conidiospores is at a peak, and unwanted mycelium was removed by two superposed 20 μm meshes. 10 ml of the filtrate was placed in a centrifuge tube, and centrifugation was performed at 1000 r.p.m. for 10 minutes. After centrifuging, the supernatant liquid was discarded and 1 ml of PD culture was added so as to obtain a suspension of conidiospores.

(10) Inoculation method using conidiospores

The Baron, Merion, Kenblue and Troy strains of Kentucky bluegrass were respectively artificially inoculated with a conidiospore suspension of FERM P-14798 using the callus inoculation method described in (8). After examining the plants obtained by the method described in (1), it was found that the endophyte had been introduced with high frequency, and there was a large significant difference compared to the inoculation method of (8) using the mycelium.

(11) Detection of endophyte by enzyme immunoassay method (ELISA)

The endophyte was detected from leaf sections of plants into which it had been introduced by the artificial inoculation methods of (7), (8) and (9) as follows.

Buffer solution was introduced into 0.5 g raw weight of the explant, and the mixture was crushed in a mortar so as to obtain an extract. 50 μl of this extract was placed in a well in a microplate, and adsorbed at room temperature for 30 minutes. Uncombined antigen was then washed out.

The well was filled with solution (3% skimmed milk solution) and washed 30 minutes later. Anti-endophyte rabbit antiserum (primary antibody) was added to the well, reacted at room temperature for 60 minutes, and uncombined antibody was washed out.

Diluted secondary antibody (antirabbit IgG, goat labelled with alkali phosphatase) was added to the well, reacted at room temperature for 60 minutes, and uncombined antibody was washed out. A basic solution was then added to the well so as to cause an alkali phosphatase reaction. The reaction was stopped by 0.5N NaOH, and the degree of light absorption at 405 nm was measured.

As a result, all specimens into which endophyte had been introduced by the methods described in (7), (8) and (9) gave a color reaction, thus proving the presence of these endophytes in Kentucky bluegrass.

(12) Resistance to webworm

Using Kentucky bluegrass (Baron strain) into which the endophyte FERM P-14798 had been introduced as described in (8) (referred to hereafter as KB-Baron 14798), resistance to webworm was examined.

KB-Baron 14798 was acclimatized at 2 months after inoculation. As a comparison, seeds of Baron which had not been inoculated were immersed in 70% ethanol for 10 seconds, immersed in 2.5% aqueous sodium hypochlorite solution for 10 minutes, washed 3 times with sterile water, dried in a current of air, transferred to an MS base culture, germinated and acclimatized after 2 months growth.

Twenty of these specimens were planted in each of 20×30×10 cm plant boxes containing a culture medium to a height of 8 cm, and monitored at room temperature for 120 days. After 120 days, webworm eggs were immersed in 70% ethanol for 10 seconds, washed 3 times with sterile water and dried in a current of air. Approx. 200 of the eggs were then placed in each plant box.

The eggs hatched after one week and began causing damage. Initially the webworm larvae damaged both KB-Baron 14798 and the comparison group, however in KB-Baron 14798 which contained endophyte the damage stopped. Consequently whereas the control group was completely ravaged in 3–4 days, KB-Baron 14798 suffered only initial damage.

(13) Resistance to curvularia spot

Drechslera sp., Curvularia sp. and Bipolaris sp. isolated from curvularia spot occurring in Kentucky bluegrass were respectively grown on a PDA culture for 2 weeks, then conidiospores formed on the surface of the colonies were removed with a needle, suspended in sterile water and the concentration was adjusted to 5000–10000/ml.

KB-Baron 14798 plants in their 2nd month after inoculation were used. As a control, seeds from Baron which had not been inoculated were immersed in 70% ethanol for 10 seconds, immersed in 2.5% aqueous sodium hypochlorite solution for 10 minutes, washed 3 times with sterile water, dried in a current of air, transferred to an MS base culture, germinated and grown for 2 months. Ten of these specimens were placed in each of 6×6×10 plant boxes containing a sterile culture medium, and grown for 2 weeks.

To inoculate the plants with pathogenic fungi, the entire surface of the plants was sprayed or coated, and the plants were grown at 28° C. for one month under 16 hour daylight conditions.

As a result, for all pathogenic fungi, leaf rot set in from the tip of the leaf from the first week after inoculation in the control group, and by the third week all the leaves of the plants had withered and died. On the other hand in the case of KB-Baron 14798 containing endophyte, although there were black spots in the initial stage of infection having a diameter of approx. 2 mm on the leaves, and curvularia spot was found up to approx. 1 cm from the tip of the leaf, there was effectively no further spreading of blotches. A significant difference was thus clearly observed with respect to curvularia spot caused by Drechslera sp., Curvularia sp. and Bipolaris sp.

(14) Resistance to rust

Summer spores formed on the leaves of Kentucky bluegrass infected with black rust were made to adhere to a moist filter paper of size 5×5 mm. The filter paper carrying the spores was placed on the leaves of KB-Baron 14798 prepared by the same method as described in (12) and of plants in a control group so as to inoculate the plants. The inoculated plants were incubated at 20° C. at high humidity in the dark for 12 hours, placed under illumination for 16 hours, and cultivated for 3 weeks.

As a result, 10 days after inoculation, clumps of summer spores were formed on the surfaces of the leaves of both KB-Baron 14798 and the control group. However, whereas in the control group the entire plant was covered with a secondary formation of many clumps of summer spores, in KB-Baron 14798 there were very few newly formed clumps and they did not cover the entire plant surface. Hence, there was clearly a significant difference in the occurrence of this disease.

What is claimed:

1. A grass selected from a group consisting of Genus Agrostis and Genus Poa not containing filamentous endophytic fungi into which filamentous endophtic fungi of Acremonium are artificially introduced, said filamentous endophytic fungi introduced into said grass are Acremonium sp. Po-001. Acremonium sp. M-004 or Acremonium sp. M-002 deposited at Japanese National Institute of Bioscience and Human Technology as FERM P-14798, FERM P-14799, or FERM P-14800.

2. A grass as defined in claim 1, wherein said endophytic fungi introduced into said grass produce an insect-resistant indole alkaloid.

3. A grass which is a bluegrass not containing filamentous endophytic fungi into which filamentous endophtic fungi selected from a group consisting of Acremonium and Epichloe are artificially introduced, said endophytic fungi introduced into said bluegrass being Acremonium sp. Po-001. Acremonium sp. Po-023 or Epichloe sp. Po-048 deposited at Japanese National Institute of Bioscience and Human Technology as FERM P-14798, FERM P-15029 or FERM P-15030.

4. A method of introducing endophytic fungi into a grass selected from a group consisting of Genus Agrostis and Genus Poa, comprising:

a step for isolating filamentous endophytic fungi of Acremonium from a plant and artificially growing the fungi, said endophytic fungi being Acremonium sp. Po-001. Acremonium sp. M-004 or Acremonium sp. M-002 deposited at Japanese National Institute of Bioscience and Human Technology as FERM P-14798, FERM P-14799 or FERM P-14800, a step for artificially inoculating the grass with said artificially grown endophytic fungi, and a step for infecting said grass with said artificially grown endophytic fungi.

5. A method of introducing endophytic fungi into a grass as defined in claim 4, wherein at least one type of endophytic fungi is introduced artificially.

6. A method of introducing endophytic fungi into a bluegrass comprising:

a step for isolating filamentous endophytic fungi selected from a group consisting of Acremonium and Epichloe from a plant and artificially growing the fungi, said endophytic fungi being Acremonium Sp. Po-001, Acremonium sp. Po-023 or Epichloe sp. Po-048 deposited at Japanese National Institute of Bioscience and Human Technology as FERM P-14798, FERM P-15029 or FERM P-15030, a step for artificially inoculating a bluegrass with said artificially grown endophytic fungi, and a step for infecting said bluegrass with said artificially grown endophytic fungi.

7. A method of introducing endophytic fungi into a bluegrass comprising:
- a step for isolating the filamentous endophytic fungi Epichloe from a plant and artificially growing the fungi,
- a step for artificially inoculating a bluegrass with conidiospores of said endophytic fungi, and
- a step for infecting said bluegrass with said artificially grown endophytic fungi.

8. A method of introducing endophytic fungi into a grass as defined in claim 6, wherein at least one type of endophytic fungi is introduced artificially.

* * * * *